(12) United States Patent
Sutton

(10) Patent No.: US 10,391,292 B2
(45) Date of Patent: Aug. 27, 2019

(54) HEMOSTASIS SEALING DEVICE WITH CONSTRICTION RING

(71) Applicant: Surmodics, Inc., Eden Prairie, MN (US)

(72) Inventor: Gregg Stuart Sutton, Orono, MN (US)

(73) Assignee: Surmodics, Inc., Eden Prairie, MN (US)

( * ) Notice: Subject to any disclaimer, the term of this patent is extended or adjusted under 35 U.S.C. 154(b) by 80 days.

(21) Appl. No.: 15/620,008

(22) Filed: Jun. 12, 2017

(65) Prior Publication Data

US 2017/0361083 A1 Dec. 21, 2017

Related U.S. Application Data

(60) Provisional application No. 62/350,354, filed on Jun. 15, 2016.

(51) Int. Cl.
*A61M 39/00* (2006.01)
*A61M 39/02* (2006.01)
(Continued)

(52) U.S. Cl.
CPC ..... *A61M 39/0613* (2013.01); *A61B 17/0057* (2013.01); *A61B 2017/00592* (2013.01); (Continued)

(58) Field of Classification Search
CPC .............. A61M 39/06; A61M 39/0613; A61B 17/0057
See application file for complete search history.

(56) References Cited

U.S. PATENT DOCUMENTS 4,973,493 A 11/1990 Guire
5,092,857 A 3/1992 Fleischhacker et al.
(Continued)

FOREIGN PATENT DOCUMENTS

EP 0143518 6/1985
WO 0012171 3/2000
(Continued)

OTHER PUBLICATIONS

US 5,520,663 A, 05/1996, Patterson et al. (withdrawn)
(Continued)

*Primary Examiner* — Edelmira Bosques
(74) *Attorney, Agent, or Firm* — Pauly, DeVries Smith & Deffner LLC

(57) ABSTRACT

Aspects herein relate to a medical device for providing a leak-resistant seal for use in a vascular access device. In various embodiments, a device for vascular access hemostasis is included. The device can include an enclosure configured to at least partially receive a medical device, the enclosure defining a cavity. The enclosure can have a first seal portion and a second seal portion, the cavity disposed between the first seal portion and the second seal portion. The enclosure can include the second seal portion comprising a split, septum seal. The enclosure can include a barrel in structural communication with the second seal portion. The device can include a constriction ring disposed around the barrel, the constriction ring interfacing with the second seal portion to limit movement of the split, septum seal.

16 Claims, 8 Drawing Sheets

(51) Int. Cl.
 *A61M 39/06* (2006.01)
 *A61B 17/00* (2006.01)

(52) U.S. Cl.
 CPC ............ *A61M 2039/0072* (2013.01); *A61M 2039/0294* (2013.01); *A61M 2039/062* (2013.01); *A61M 2039/064* (2013.01); *A61M 2039/068* (2013.01); *A61M 2039/0626* (2013.01); *A61M 2039/0653* (2013.01); *A61M 2039/0673* (2013.01)

(56) References Cited

U.S. PATENT DOCUMENTS

| | | |
|---|---|---|
| 5,114,408 A | 5/1992 | Fleischhaker et al. |
| 5,125,903 A | 6/1992 | Mclaughlin et al. |
| 5,195,980 A | 3/1993 | Catlin |
| 5,207,649 A | 5/1993 | Aruny |
| 5,269,764 A | 12/1993 | Vetter et al. |
| 5,300,033 A | 4/1994 | Miller |
| 5,304,156 A | 4/1994 | Sylvanowicz et al. |
| 5,324,271 A | 6/1994 | Abiuso et al. |
| 5,336,192 A | 8/1994 | Palestrant |
| 5,414,075 A | 5/1995 | Swan et al. |
| 5,453,095 A | 9/1995 | Davila et al. |
| 5,456,284 A | 10/1995 | Ryan et al. |
| 5,507,732 A | 4/1996 | Mcclure et al. |
| 5,520,655 A | 5/1996 | Davila et al. |
| 5,549,576 A | 8/1996 | Patterson et al. |
| 5,603,702 A | 2/1997 | Smith et al. |
| 5,613,956 A | 3/1997 | Patterson et al. |
| 5,637,460 A | 6/1997 | Swan et al. |
| 5,643,227 A | 7/1997 | Stevens |
| 5,702,370 A | 12/1997 | Sylvanowicz et al. |
| 5,714,360 A | 2/1998 | Swan et al. |
| 5,748,318 A | 5/1998 | Maris et al. |
| 5,858,007 A | 1/1999 | Fagan et al. |
| 5,858,653 A | 1/1999 | Duran et al. |
| 5,935,112 A | 8/1999 | Stevens et al. |
| 6,007,833 A | 12/1999 | Chudzik et al. |
| 6,024,729 A | 2/2000 | Dehdashtian et al. |
| 6,053,861 A | 4/2000 | Grossi et al. |
| 6,077,698 A | 6/2000 | Swan et al. |
| 6,086,570 A | 7/2000 | Aboul-Hosn et al. |
| 6,142,981 A | 11/2000 | Heck et al. |
| 6,278,018 B1 | 8/2001 | Swan |
| 6,465,178 B2 | 10/2002 | Chappa et al. |
| 6,514,734 B1 | 2/2003 | Clapper et al. |
| 6,551,283 B1 | 4/2003 | Guo et al. |
| 6,569,120 B1 | 5/2003 | Cuny et al. |
| 6,603,040 B1 | 8/2003 | Swan |
| 6,632,200 B2 | 10/2003 | Guo et al. |
| 6,702,255 B2 | 3/2004 | Dehdashtian |
| 6,712,791 B2 | 3/2004 | Lui et al. |
| 6,762,019 B2 | 7/2004 | Swan et al. |
| 7,081,106 B1 | 7/2006 | Guo et al. |
| 7,101,353 B2 | 9/2006 | Lui et al. |
| 7,138,541 B2 | 11/2006 | Swan |
| 7,241,276 B2 | 7/2007 | Argentine et al. |
| 7,309,593 B2 | 12/2007 | Ofstead et al. |
| 7,348,055 B2 | 3/2008 | Chappa et al. |
| 7,582,070 B2 | 9/2009 | Goode et al. |
| 7,628,774 B2 | 12/2009 | Fangrow et al. |
| 7,731,694 B2 | 6/2010 | Becker et al. |
| 7,736,689 B2 | 6/2010 | Chappa et al. |
| 7,807,750 B2 | 10/2010 | Taton et al. |
| 7,901,379 B2 | 3/2011 | Argentine et al. |
| 7,976,503 B2 | 7/2011 | Khan et al. |
| 8,016,791 B2 | 9/2011 | Sugiki et al. |
| 8,039,524 B2 | 10/2011 | Ralph et al. |
| 8,048,033 B2 | 11/2011 | Becker et al. |
| 8,096,976 B2 | 1/2012 | Sugiki et al. |
| 8,137,321 B2 | 3/2012 | Argentine et al. |
| 8,177,760 B2 | 5/2012 | Rome et al. |
| 8,246,585 B2 | 8/2012 | Schennib et al. |
| 8,273,059 B2 | 9/2012 | Nardeo et al. |
| 8,444,628 B2 | 5/2013 | Fangrow, Jr. |
| 8,487,137 B2 | 7/2013 | Guire et al. |
| 8,523,822 B2 | 9/2013 | Nardeo et al. |
| 8,790,309 B2 | 7/2014 | Goode et al. |
| 8,809,411 B2 | 8/2014 | Rooijmans |
| 8,870,850 B2 | 10/2014 | Fangrow et al. |
| 8,889,760 B2 | 11/2014 | Kurdyumov et al. |
| 8,932,694 B2 | 1/2015 | Rolfes Meyering |
| 9,005,172 B2 | 4/2015 | Chung |
| 9,410,044 B2 | 8/2016 | Kurdyumov |
| 9,522,266 B2 | 12/2016 | Sutton et al. |
| 2003/0050604 A1 | 3/2003 | Lui et al. |
| 2004/0260243 A1 | 12/2004 | Rickerd |
| 2005/0020981 A1 | 1/2005 | Kurth et al. |
| 2007/0032882 A1 | 2/2007 | Lodhi et al. |
| 2009/0012476 A1 | 1/2009 | Catlin |
| 2009/0209914 A1* | 8/2009 | Koch ..................... 604/167.02 |
| 2009/0259175 A1 | 10/2009 | Nordgren |
| 2010/0198168 A1 | 8/2010 | Rooijmans |
| 2010/0241078 A1 | 9/2010 | Barnes |
| 2010/0292638 A1 | 11/2010 | Becker et al. |
| 2010/0331784 A1 | 12/2010 | Fisher et al. |
| 2011/0040260 A1 | 2/2011 | Leeflang et al. |
| 2011/0144373 A1 | 6/2011 | Swan et al. |
| 2012/0148852 A1 | 6/2012 | Jelle et al. |
| 2012/0149934 A1 | 6/2012 | Kurdyumov |
| 2012/0221024 A1 | 8/2012 | Sutton et al. |
| 2012/0245527 A1 | 9/2012 | Stephens et al. |
| 2012/0296274 A1 | 11/2012 | Slager |
| 2013/0143056 A1 | 6/2013 | Swan et al. |
| 2014/0343512 A1 | 11/2014 | Fischer et al. |
| 2015/0140107 A1 | 5/2015 | Slager et al. |
| 2015/0157843 A1 | 6/2015 | Pepin et al. |
| 2016/0175489 A1 | 6/2016 | Babcock et al. |
| 2018/0169396 A1 | 6/2018 | Olson |

FOREIGN PATENT DOCUMENTS

| | | |
|---|---|---|
| WO | 2007044879 | 4/2007 |
| WO | 2010087943 | 7/2011 |
| WO | 2012118852 | 9/2012 |
| WO | 2017218634 | 12/2017 |
| WO | 2018112031 | 6/2018 |

OTHER PUBLICATIONS

"International Search Report and Written Opinion," for PCT Application No. PCT/US2017/037410 dated Sep. 25, 2017 (11 pages).
"International Search Report and Written Opinion," for PCT Application No. PCT/US2017/066091 dated Mar. 20, 2018 (14 pages).
"International Preliminary Report on Patentability," for PCT/US2012/027012, dated Sep. 12, 2013 (5 pages).
"International Search Report and Written Opinion," for PCT Application No. PCT/US2012/027012), dated Sep. 28, 2012 (9 pages).
"International Preliminary Report on Patentability," for PCT Application No. PCT/US2017/037410 dated Dec. 27, 2018 (8 pages).

* cited by examiner

HEMOSTASIS SEALING DEVICE WITH CONSTRICTION RING

This application claims the benefit of U.S. Provisional Application No. 62/350,354, filed Jun. 15, 2016, the contents of which are herein incorporated by reference.

FIELD

Aspects herein relate to a medical device for providing a leak-resistant seal for use in a vascular access device.

BACKGROUND

When interventional catheter devices are inserted into the vascular system, the physician usually starts with a needle stick, followed by dilating the artery in order to insert an introducer sheath device that is left in place for the duration of the procedure. This introducer sheath acts as the main conduit for entry of subsequent therapeutic or diagnostic devices. In most instances, these introducer sheaths contain a hemostatic component that restricts back-flow of blood from the artery. These hemostasis seals are generally passive and provide sealing around the catheter devices and guide wires that are used during the procedure.

SUMMARY

Aspects herein relate to a medical device for providing a leak-resistant seal for use in a vascular access device. In various embodiments, a device for vascular access hemostasis is included. The device can include an enclosure configured to at least partially receive a medical device, the enclosure defining a cavity. The enclosure can have a first seal portion and a second seal portion, the cavity disposed between the first seal portion and the second seal portion. The enclosure can include the second seal portion comprising a split, septum seal. The enclosure can include a barrel in structural communication with the second seal portion. The device can include a constriction ring disposed around the barrel, the constriction ring interfacing with the second seal portion to limit movement of the split, septum seal.

In various embodiments, a sealing device is included, the sealing device including a device enclosure defining a cavity, wherein the device enclosure is configured to compressively interface with a housing. The sealing device can further include a first seal portion in communication with the device enclosure, the first seal portion defining an opening; a second seal portion in communication with the device enclosure, the second seal portion defining a split; and a constriction ring disposed around the device enclosure, the constriction ring disposed over the split of the second seal portion.

In some embodiments, a method of making a sealing device is included. The method can include obtaining an enclosure configured to at least partially receive a medical device. The enclosure can define a cavity and can have a first seal portion and a second seal portion, the cavity disposed between the first seal portion and the second seal portion. The second seal portion can include a split, septum seal. The method can further include disposing a constriction ring around the enclosure, the constriction ring interfacing with the split, septum seal to limit movement of the split, septum seal.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE DRAWINGS

Aspects herein can be more completely understood in consideration of the following detailed description of various embodiments in connection with the accompanying drawings, in which.

These drawings are to be considered general representations of some embodiments, and it will be appreciated that they are not drawn to encompass all embodiments, nor are they always drawn to scale. While aspects herein are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope of that described herein.

DETAILED DESCRIPTION

Current hemostasis valves have limited performance when they are made for large size devices. This is due to the extreme size difference between the large catheter device and the much smaller guide wire used in these procedures. When larger catheter devices are used (such as 14-20 Fr), it can be difficult to seal on both this large diameter and on the guide wires used in these types of procedures, which are generally only 0.035" in diameter. Current valves tend to leak when only the guide wire is in place or when nothing is in place, especially after large diameter devices have passage through the sealing device and have stretched or damaged the seal in the process.

Aspects herein are directed to a device for vascular access, in particular a hemostasis sealing devices that accommodate substantial size differences between relatively large catheter devices and small guide wires with enhanced sealing performance. Hemostasis sealing devices herein can include a first seal portion for device sealing and a second seal portion for guide wire sealing. As a vascular access device is passed over a guide wire during a procedure, the device passes through a first seal portion which stretches and seals around the medical device. While the second seal portion is generally configured for guide wire sealing, a split defined by the second seal portion allows passage of relatively large bore devices.

Hemostasis sealing valves herein can also include a constriction ring that interfaces (directly or indirectly) with the second seal portion to provide enhanced sealing properties of the second seal portion.

The first seal portion can be a hole seal or a wring seal, while the second seal portion can be a split, septum seal. The hemostasis sealing device generally has structural elements that are configured to structurally support the second seal portion for sealing. In a variety of embodiments, the second seal portion is held in compression by a housing that compressively interfaces with the hemostasis sealing device. In such an embodiment, support ribs can be in compressive communication with the second seal portion. The split of the second seal portion can be an axial split offset from the support ribs. In some implementations a barrel extends from the second seal portion to inhibit seal inversion or misalignment.

Figure 1:
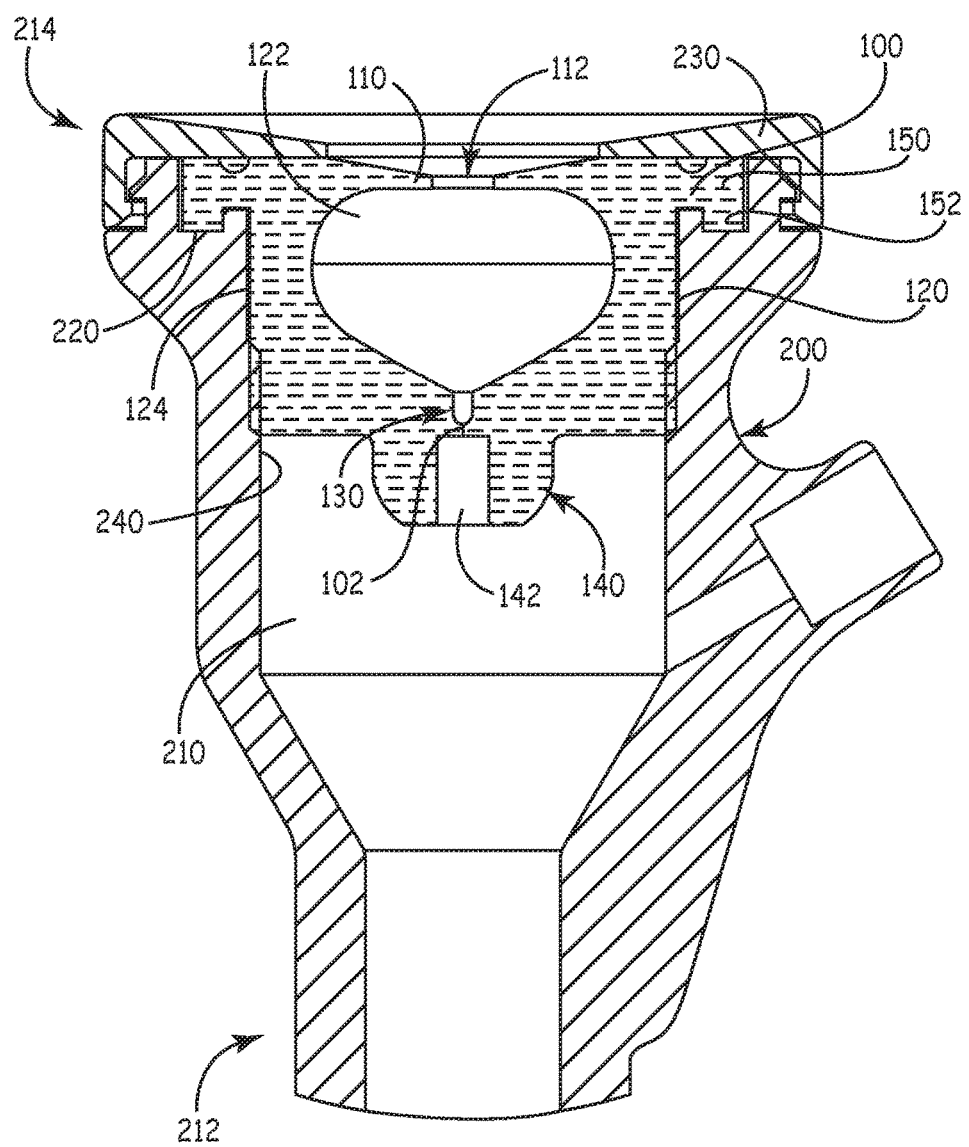
FIG. 1 is a cross-sectional view of an example hemostasis sealing device consistent with the technology disclosed herein.

An example embodiment of such a hemostasis sealing device is shown in FIG. 1. The hemostasis sealing device 100 is disposed in a housing 200 and has a device enclosure 120 in communication with a first seal portion 110 on a support ring 150, a second seal portion 130, and a barrel 140. The housing 200 is generally an introducer sheath, but could be another device that is generally rigid and defines a passageway 210 extending from the proximal end 214 of the housing 200 to a distal end 212 of the housing 200.

The hemostasis sealing device 100 is generally configured to provide a fluid seal for vascular access devices and simultaneously allowing translation or movement of a guide wire while providing a fluid seal there-around. The hemostasis sealing device 100 can be constructed of a variety of materials such as, for example, silicone rubber in the range of 10-60 Shore A durometer. In another example, the hemostasis sealing device 100 can be constructed so as to contain nitinol elements. Those having skill in the art will recognize that the hemostasis sealing device 100 can be constructed of various thermoplastic elastomers, and combinations thereof, available and known.

The hemostasis sealing device 100 is configured to be received by the proximal end 214 of the housing 200. In at least one embodiment the hemostasis sealing device 100 is in compression upon being received by the housing 200. In one embodiment the compression of the hemostasis sealing device 100 is in the range of 0-5% of the diameter of the seal body. This compression allows the hemostasis sealing device 100 to be firmly held within the housing 200.

The hemostasis sealing device 100 has a device enclosure 120 defining a device cavity 122 and, as mentioned above, has the first seal portion 110 and the second seal portion 130. The first seal portion 110 is generally configured to provide a seal for a medical device passing into the device cavity 122, such as a vascular access device, and the second seal portion 130 is generally configured to provide a seal for a guide wire. The device cavity 122 is generally sized to receive at least a portion of the medical device.

In this particular embodiment, the support ring 150 has a radial flange 152 and is received by a ring receptacle 220 defined by the housing 200. In some embodiments, the support ring 150 will be relatively rigid compared to some portions of the hemostasis sealing device 100. An outer annular surface 124 of the hemostasis sealing device 100 is received by the proximal end 214 of the passageway 210 of the housing 200. In at least one embodiment, the housing 200 exerts compressive force on the outer annular surface 124 of the hemostasis sealing device 100.

The first seal portion 110 is generally elastomeric and defines a first seal opening 112 that is sized to seal around the medical device passing there-through. In one embodiment, the first seal portion 110 is a sealing hole. In another embodiment, the first seal portion 110 is a sealing ring. Typically the first seal opening 112 defined by the first seal portion 110 is sized in the range of 0.2-0.4 times the diameter of the largest device size that is to be inserted through a given seal. For instance, for a 20Fr device (0.260 in. diameter), the first seal opening 112 size would be in the range of 0.052-0.104 in. in diameter.

The second seal portion 130 is similarly elastomeric to the first seal portion 110 and defines a split 102 there-through. The split 102 will generally be axial relative to the second seal portion 130, and can also be axial relative to the hemostasis sealing device 100 itself. In a variety of embodiments, the second seal portion 130 has a thickness in the range of 0.005-0.020 inches and a diameter in the range of 0.9-1.3 times the diameter of the guide wire to be used. Given the size differential between the first seal portion 110 and the second seal portion 130, in the current embodiment, the cross section of the device cavity 122 generally tapers towards the second seal portion 130. Those having skill in the art will recognize that the second seal portion 130 can be consistent with a split septum seal. In a variety of embodiments, structural elements of the hemostasis sealing device 100 are configured to provide structural support to the second seal portion 130. As one example, the compression fit between the hemostasis sealing device 100 and the housing 200 compresses the second seal portion 130 at the split 102 to be in sealing engagement with a guide wire.

A barrel 140 of the hemostasis sealing device 100 generally extends from the second seal portion 130. The barrel 140 is generally annular and coaxial with the second seal portion 130. The barrel 140 defines a barrel opening 142, a substantial portion of which is cylindrical in shape. The barrel 140 is generally configured to provide structural support to the second seal portion 130. In at least one embodiment, the barrel 140 prevents the split 102 of the second seal portion 130 from becoming misaligned and/or inverted on itself, wherein misalignment and inversion can inhibit complete sealing.

Figure 2:
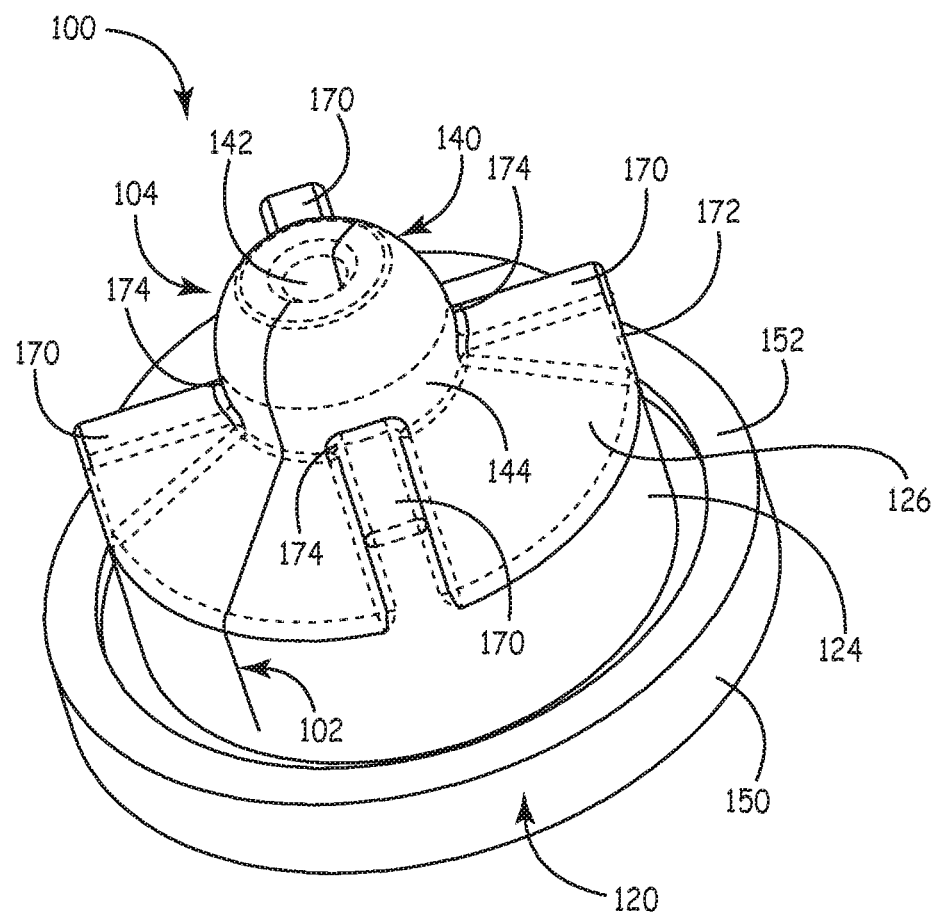
FIG. 2 is a perspective view of an example hemostasis sealing device consistent with the technology disclosed herein.

FIG. 2 depicts a perspective view of the hemostasis sealing device 100 of FIG. 1. From this view the overall configuration of the split is more clearly visible and the outer configuration of the device enclosure 120 and the support ribs 170 are visible.

The split 102 is generally defined from the distal end 104 of the hemostasis sealing device 100, through the barrel 140 and the device enclosure 120, and extending towards the support ring 150. In a variety of embodiments the split 102 does not extend through the support ring 150 or the first seal portion 110. In a variety of implementations, it can be desirable for the hemostasis sealing device 100 to allow passage of large-bore devices, and the split 102 defined by the hemostasis sealing device 100 can accommodate such a use.

A tapered portion 126 of the device enclosure 120 extends between the outer annular surface 124 of the device enclosure 120 and the barrel 140. The tapered portion 126 can generally correspond with the tapered shape of the device cavity 122 and can extend adjacent to the second seal portion 130 (See FIG. 1). In the current embodiment the tapered portion 126, the annular surface 124, and the barrel 140 are a single cohesive unit. In some embodiments the annular surface 124, the barrel 140, and the tapered portion 126 can be an assembly of multiple components.

In a variety of implementations the hemostasis sealing device 100 includes two or more support ribs 170 along the tapered portion 126 of the device enclosure 120 in compressive communication with at least a portion of the split 102. As depicted in FIG. 2, the current embodiment has four support ribs 170. The support ribs 170 are generally configured to provide structural support to the hemostasis sealing device 100 when the hemostasis sealing device 100 is installed in a housing, such as the housing depicted in FIG. 1. The support ribs 170 can provide structural support to the hemostasis sealing device 100 particularly along the split 102 to ensure sealing of the second seal portion 130 (visible in FIG. 1) despite insertion of a medical device in the device enclosure 120.

In the current embodiment, an outer end surface 172 of each support rib 170 is coplanar with the outer annular surface 124 of the device enclosure 120. As such, the outer annular surface 124 of the device enclosure 120, the outer end surface 172 of each support rib 170 is configured for compressive interfacing with the inner annular surface 240 of the housing 200 (See FIG. 1). An inner end 174 of each support rib 170 contacts the outer surface 144 of the barrel 140, which can be adjacent to the second seal portion 130 (See FIG. 1). As such, despite expansion forces from the device cavity 122 and the first seal opening 112 (See FIG. 1) on the hemostasis sealing device 100 upon medical device insertion, reactive compressive forces by the housing 200 are exerted, in part, on the support ribs 170 and transferred to the barrel 140 and, therefore, around the second seal portion 130 of the hemostasis sealing device 100. Such compressive forces can prevent separation of the hemostasis sealing device 100 at least around the second seal portion 130.

It can be desirable to stagger the split 102 defined by the hemostasis sealing device 100 relative to the support ribs 170 such that relatively symmetrical compressive forces are applied about the second seal portion 130. In the current embodiment, the support ribs 170 are symmetrical relative to the split 102. The split 102 is offset from the support ribs 170 by about 45 degrees. Other configurations of support ribs relative to a split defined by a hemostasis sealing device are also possible.

Figure 3:
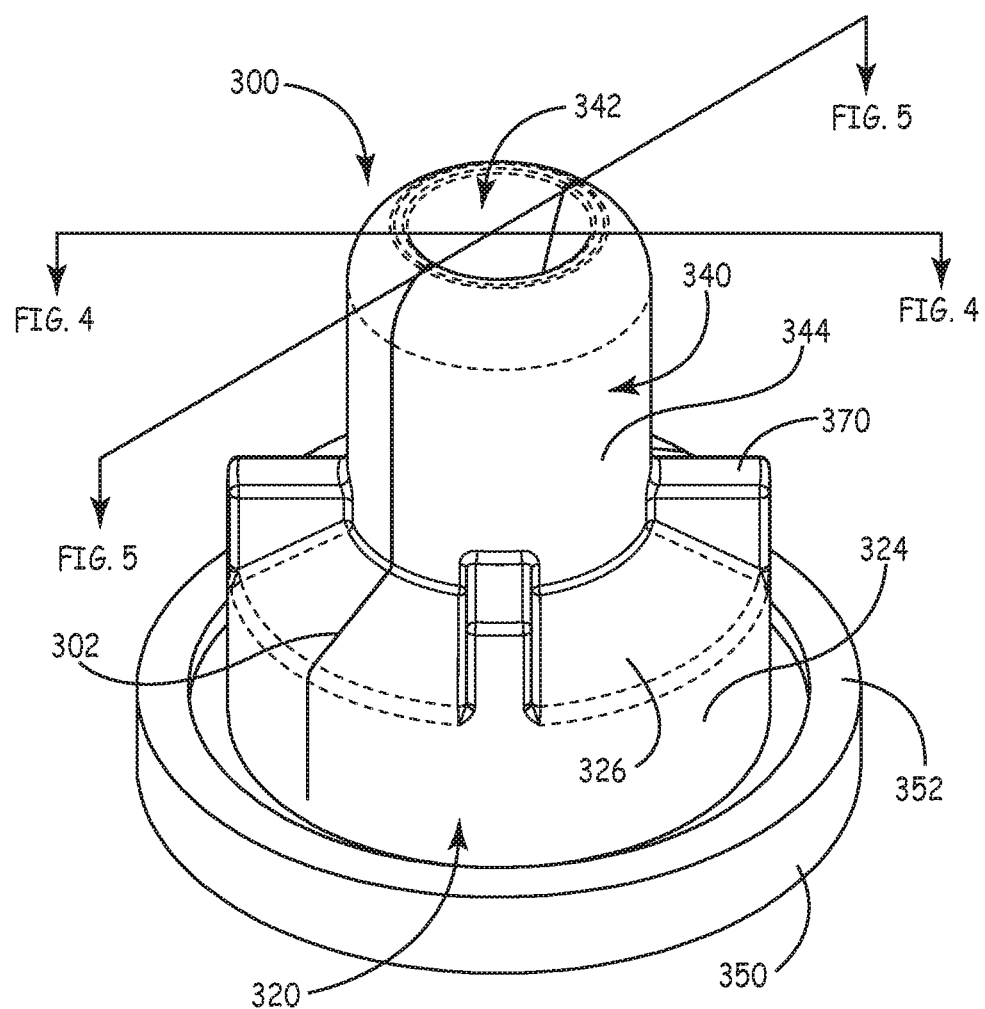
FIG. 3 is a perspective view of another example hemostasis sealing device consistent with the technology disclosed herein.

FIG. 3 is a perspective view of another embodiment of a hemostasis sealing device consistent with the technology disclosed herein. Similar to the hemostasis sealing device 100 depicted in FIG. 2, this hemostasis sealing device 300 has a device enclosure 320 with a first sealing portion and a second sealing portion (not visible in this view). The hemostasis sealing device 100 has a support ring 350 having a flange 352 coupled to the device enclosure 320 that has an outer annular surface 324 and a tapered portion 326. A barrel 340 defining an opening 342 is coupled to the tapered portion 326 and support ribs 370 extend along the tapered portion 326 from the outer annular surface 324 of the device enclosure 320 to the outer surface 344 of the barrel 340. A split 302 is defined by the hemostasis sealing device 300 from the distal end 304 of the hemostasis sealing device 300 towards the support ring 350. The split 302 generally extends through the barrel 340 and the device enclosure 320.

Figure 4:
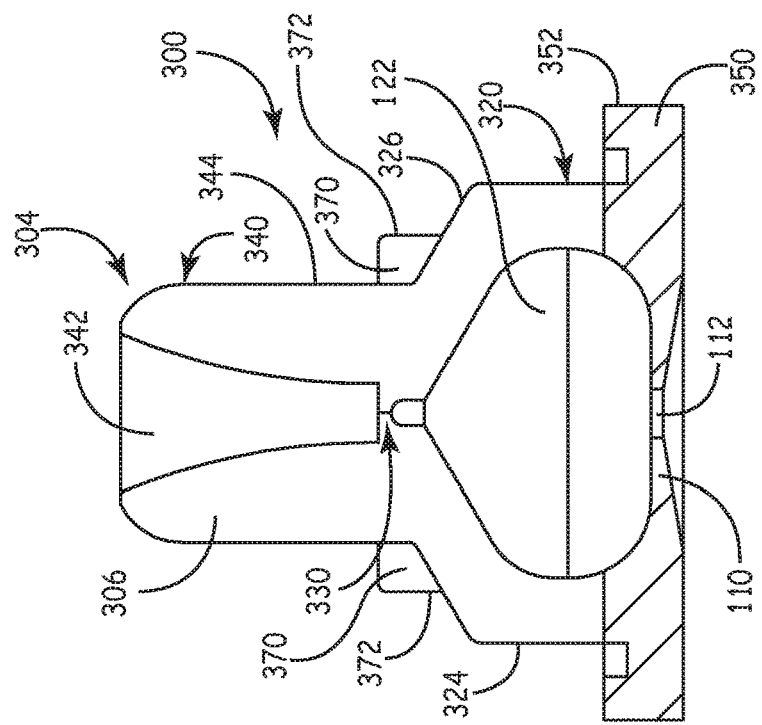
FIG. 4 is a cross-sectional view of the hemostasis sealing device of FIG. 3.
Figure 5:
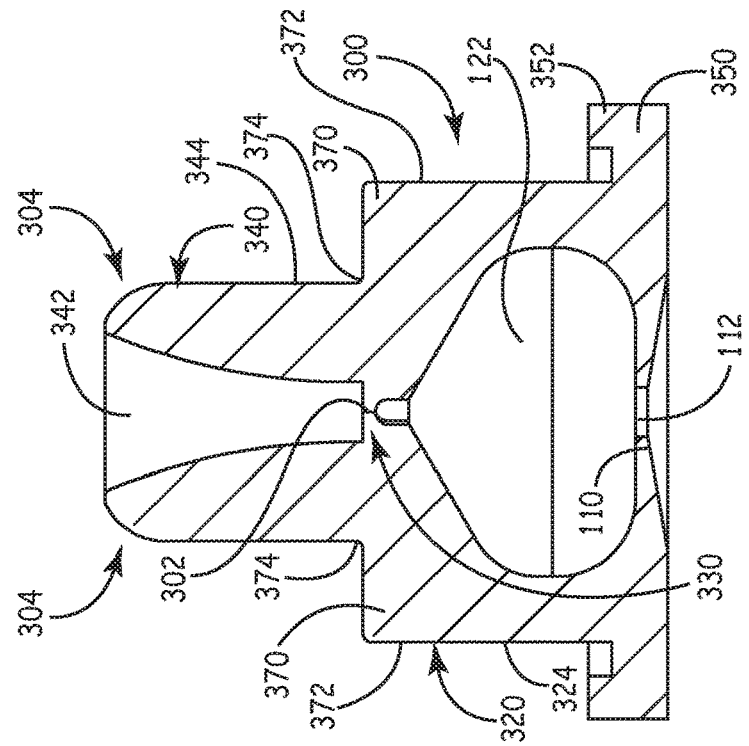
FIG. 5 is another cross-sectional view of the hemostasis sealing device of FIG. 3.

FIGS. 4 and 5 are cross-sectional views consistent with the hemostasis sealing device 300 of FIG. 3, as notated on FIG. 3. Specifically, FIG. 4 is a cross-sectional view of the hemostasis sealing device 300 through opposing support ribs 370. FIG. 5 is a cross-sectional view of the hemostasis sealing device 300 along the split 302 (See FIG. 3) revealing a split-defining surface 306 of the hemostasis sealing device 300 that is adjacent to the split 302 (FIG. 3). In FIG. 5 it is visible that the split-defining surface 306 and, therefore, the split 302 itself, extends from the distal end 304 of the hemostasis sealing device 300, through the barrel 340 and the device enclosure 320 to the support ring 350. In the current embodiment the support ring 350 does not define any portion of the split 302.

Visible in FIG. 5, the annular surface 324 of the device enclosure 320 has a tapered portion 326 that couples to the barrel 340. Similar to the embodiment depicted in FIGS. 1-2, the support ribs 370 of the hemostasis sealing device 300 of FIGS. 3-5 are disposed along the tapered portion 326 and each have an outer end surface 372 that is substantially coplanar with the outer annular surface 324 of the device enclosure 320 and an inner end 374 adjacent to the second sealing portion 330. The inner end 374 of each rib 370 generally meets the outer surface 344 of the barrel 340. There are four support ribs 370 in this particular embodiment, which are staggered 45 degrees from the split 302.

In the embodiment depicted in FIGS. 4 and 5, the barrel opening 342 defined by the barrel 340 is at least partially tapered from the second seal portion 330 to the distal end 304 of the hemostasis sealing device 300. Such a configuration can help prevent inversion of the second seal portion 330. Those having skill in the art will appreciate other configurations that could have similar advantages regarding the second seal portion 330.

Figure 6:
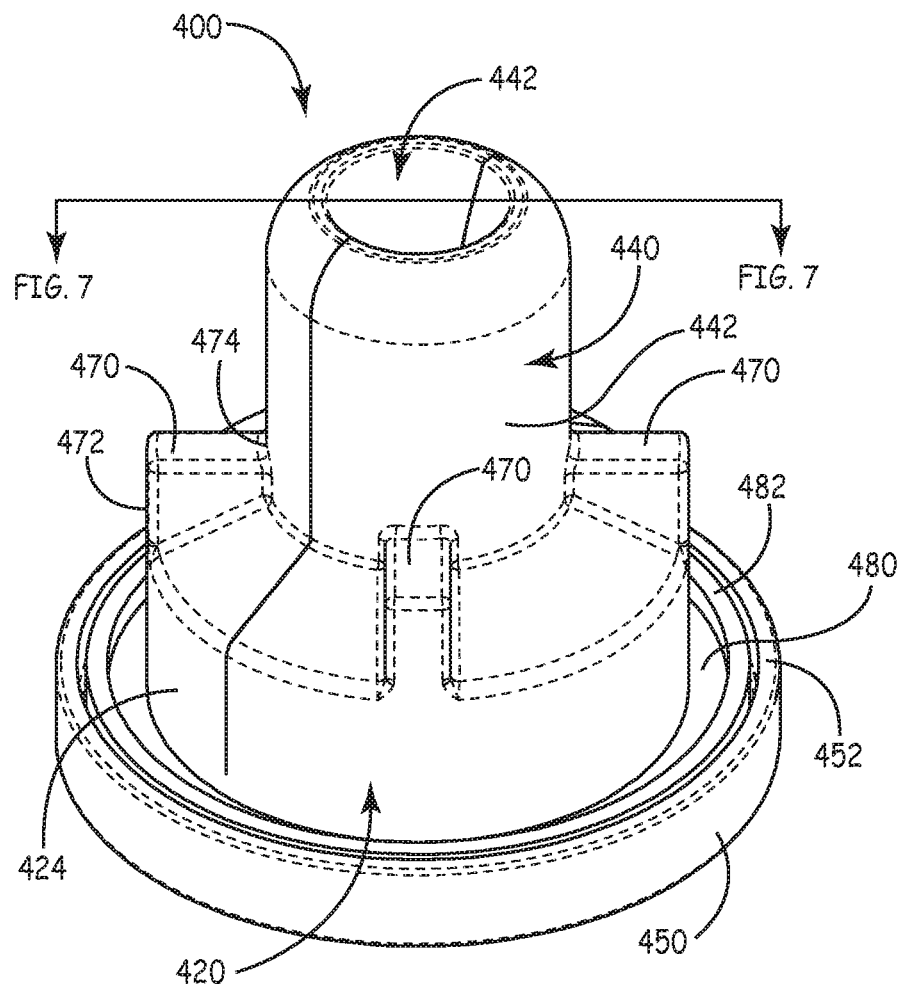
FIG. 6 is a perspective view of another example hemostasis sealing device consistent with the technology disclosed herein.
Figure 7:
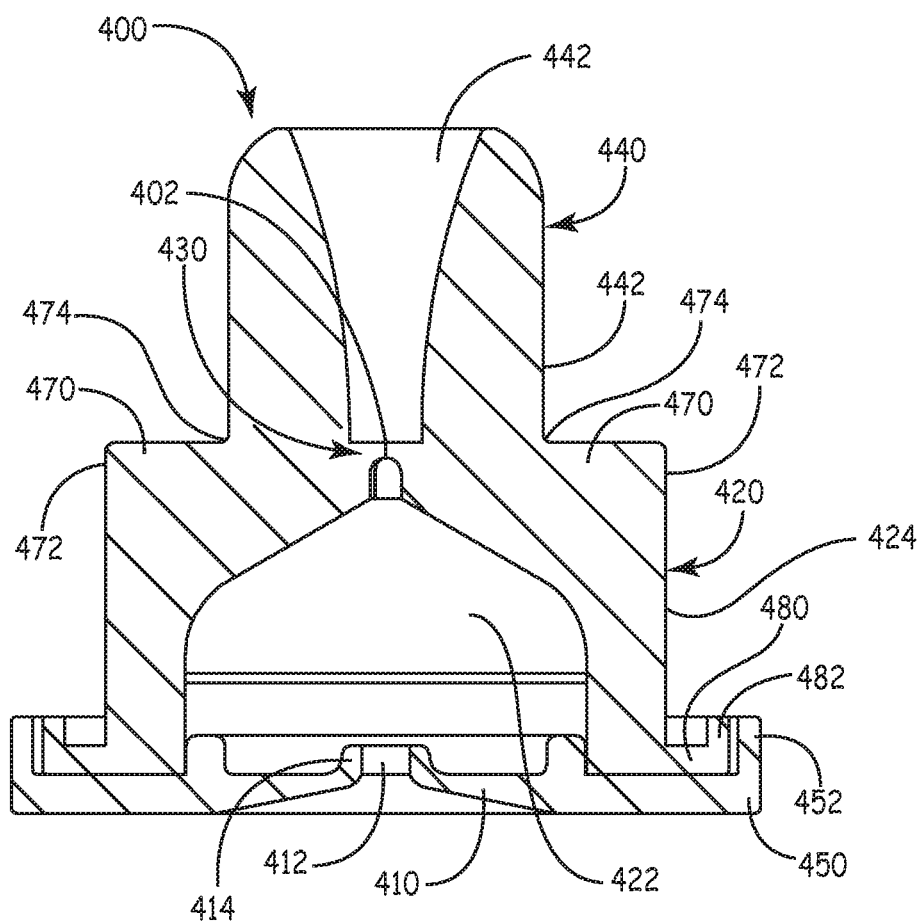
FIG. 7 is a cross-sectional view of the hemostasis sealing device of FIG. 6.

FIG. 6 is a perspective view of another embodiment of a hemostasis sealing device consistent with the technology disclosed herein. FIG. 7 is a cross-sectional view of the hemostasis sealing device 400 of FIG. 6. In this embodiment a first seal portion 410 and the second seal portion 430 are manufactured as separate components and are coupled to form a cohesive unit. The first seal portion 410 is defined by a support ring 450 having a flange 452 that is configured to engage a device enclosure 420 defining the second seal portion 430. A barrel 440 extends from the device enclosure 420 and is configured to provide structural support to the second seal portion 430. Support ribs 470 are additionally configured to provide structural support to the second seal portion 430. Each support rib 470 has an outer end surface 472 that is substantially coplanar with the outer annular surface 424 of the device enclosure 420 and an inner end 474 in compressive communication with the second seal portion 430. Each support rib 470 is configured to exert compressive force on the second seal portion 430, through the barrel outer surface 442, upon insertion of the hemostasis sealing device 400 in a housing such as an introducer sheath.

In the current embodiment the first seal portion 410 has a radial lip 414 extending into the device cavity 422 that at least partially defines a first seal opening 412. The radial lip 414 is generally configured to contribute to device sealing around a medical device.

The support ring 450 can be coupled to the device enclosure 420 through a variety of ways that will be known in the art. In one embodiment an adhesive is disposed between the support ring 450 and the device enclosure 420 to couple the components. In another embodiment the support ring flange 452 threadably engages a mating structure 480 defined by the device enclosure 420. The mating structure 480 can include a mating flange 482 that is configured to be concentric to the flange 452 of the support ring 450. The mating flange 482 can define a threaded surface that is configured to be received by the support ring flange 452. In some embodiments the support ring 450 is configured to be permanently fixed to the device enclosure 460. In other embodiments the support ring 450 is configured to be removably fixed to the device enclosure 460. Other configurations will be appreciated by those having skill in the art.

Figure 8:
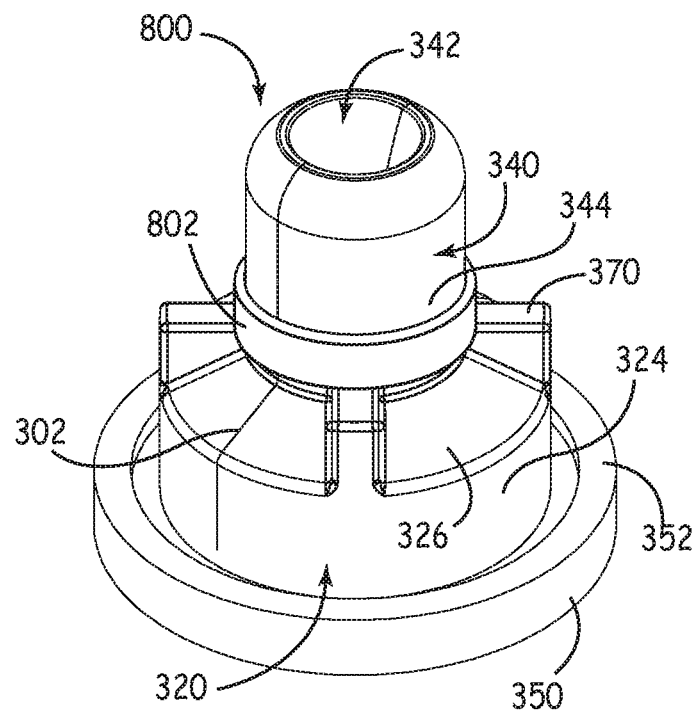
FIG. 8 is a perspective view of a hemostasis sealing device in accordance with various other embodiments.

Referring now to FIG. 8, a perspective view is shown of a hemostasis sealing device in accordance with various other embodiments. The hemostasis sealing device 800 has a device enclosure 320 with a first sealing portion and a second sealing portion (not visible in this view). The hemostasis sealing device 800 has a support ring 350 having a flange 352 coupled to the device enclosure 320 that has an outer annular surface 324 and a tapered portion 326. A barrel 340 defining an opening 342 is coupled to the tapered portion 326 and support ribs 370 extend along the tapered portion 326 from the outer annular surface 324 of the device enclosure 320 to the outer surface 344 of the barrel 340. A split 302 is defined by the hemostasis sealing device 300 from the distal end 304 of the hemostasis sealing device 300 towards the support ring 350. The split 302 generally extends through the barrel 340 and the device enclosure 320.

The hemostasis sealing device includes a constriction ring 802 that is disposed around the barrel 340. In some embodiments, the constriction ring 802 is disposed around the barrel 340 between the support ribs 370 and the distal end 304.

The constriction ring 802 can interface with the second seal portion to limit movement of the split, septum seal. The constriction ring 802 can be formed of various materials. In some embodiments, the constriction ring 802 includes an elastomeric material, such as an elastomeric polymer. In some embodiments, the constriction ring 802 can be formed of the same material as the barrel 340. In other embodiments, the constriction ring 802 and the barrel 340 are formed of two different materials. In some embodiments, the constriction ring 802 can be sized with an inner diameter (while unstretched) that is approximately equal to the outer diameter of the portion of the barrel 340 that it directly contacts. In other embodiments, the constriction ring 802 can be sized with an inner diameter (while unstretched) that is slightly smaller than the outer diameter of the portion of the barrel 340 that it directly contacts, such that it exerts a compressive force on the barrel 340 continuously.

In some embodiments, the barrel 340 does not include surface features to aid in retaining the constriction ring 802. However, in other embodiments, the surface of the barrel 340 can define a channel or notch into which the constriction ring 802 fits. In some embodiments, the barrel 340 can include a retaining flange on the surface thereof in order to help retain the constriction ring 802 in position Referring now to FIG. 9, a cross-sectional view is shown of the hemostasis sealing device 800 of FIG. 8. In this view, it can be seen that the barrel 340 defines a notch (or channel) 904, into which the constriction ring 802 fits. The notch 904 can be disposed around the outer perimeter of the barrel and can be configured to receive the constriction ring 802. Referring to now to FIG. 10, a cross-sectional view is shown of the hemostasis sealing device 800 of FIG. 8. A retaining flange 1008 is disposed on the surface of the barrel 340. In some cases, the barrel itself can define a retaining flange around the outer perimeter of the barrel. The retaining flange 1008 can be disposed between the constriction ring 802 and the distal end 304.

It will be appreciated that in some embodiments, the hemostasis sealing device 800 can include both a notch and a retaining flange.

Figure 9:
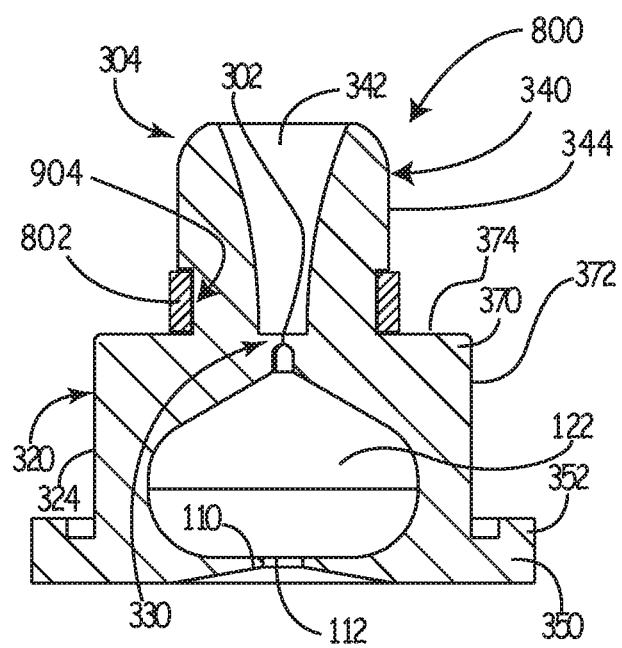
FIG. 9 is a cross-sectional view of the hemostasis sealing device of FIG. 8.
Figure 10:
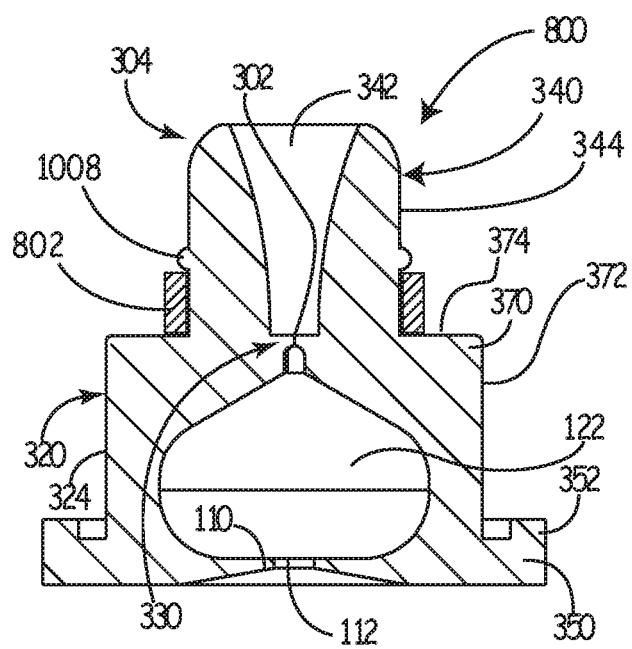
FIG. 10 is a cross-sectional view of a hemostasis sealing device in accordance with various embodiments.

Although the constriction ring 802 as shown in FIGS. 8-10 is substantially polygonal in cross-section (and rectangular in particular), the constriction ring 802 can take on many different shapes in cross-section. For example, the constriction ring 802 can also be square, non-polygonal (such as circular or oval), irregular, or the like.

In some embodiments, a method of making a sealing device is included. The method can include obtaining an enclosure configured to at least partially receive a medical device. The enclosure can define a cavity and can have a first seal portion and a second seal portion, the cavity disposed between the first seal portion and the second seal portion. The second seal portion can include a split, septum seal. The method can further include disposing a constriction ring around the enclosure, the constriction ring interfacing with the split, septum seal to limit movement of the split, septum seal.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

Aspects have been described with reference to various specific and preferred embodiments and techniques. However, it should be understood that many variations and modifications may be made while remaining within the spirit and scope herein.

The claims are:

1. A device for vascular access hemostasis, the device comprising:
   an enclosure configured to at least partially receive a medical device, the enclosure defining a cavity and having
      a distal end;
      a proximal end;
      a first seal portion;
      a second seal portion, the cavity disposed between the first seal portion and the second seal portion; and
      a plurality of support ribs operably connected to the second seal portion;
   a barrel in structural communication with the second seal portion; and a constriction ring disposed around the barrel, the constriction ring interfacing with the second seal portion to limit movement of the second seal portion;
wherein the constriction ring is disposed around the barrel between the support ribs and the distal end.

2. The device of claim 1, wherein the support ribs are configured for compressive interfacing with a housing.

3. The device of claim 1, the barrel defining a notch around the outer perimeter of the barrel, the notch configured to receive the constriction ring.

4. The device of claim 1, the barrel defining a retaining flange around the outer perimeter of the barrel.

5. The device of claim 4, wherein the retaining flange is disposed between the constriction ring and the distal end.

6. The device of claim 1, the constriction ring comprising a polygonal shape in cross-sectional.

7. The device of claim 1, the constriction ring comprising a non-polygonal shape in cross-sectional.

8. The device of claim 1, the constriction ring comprising an elastomeric material.

9. The device of claim 1, wherein the first seal portion comprises a hole seal.

10. The device of claim 1, wherein the first seal portion comprises a ring seal.

11. The device of claim 1, wherein the second seal portion is configured to be held in compression by a mating housing.

12. The device of claim 1, wherein the second seal portion defines a single axial split 45 degrees offset from the plurality of support ribs.

13. A sealing device comprising:
a device enclosure defining a cavity, the device enclosure comprising a distal end and a proximal end, wherein the device enclosure is configured to compressively interface with a housing,
a first seal portion in communication with the device enclosure, the first seal portion defining an opening;
a second seal portion in communication with the device enclosure, the second seal portion defining a split;
a plurality of support ribs operably connected to the second seal portion; and
a constriction ring disposed around the device enclosure, the constriction ring disposed over the split of the second seal portion and disposed between the support ribs and the distal end.

14. The sealing device of claim 13, the plurality of support ribs in compressive communication with the second seal portion.

15. The sealing device of claim 14, wherein the plurality of support ribs are offset from the split by about 45 degrees.

16. The sealing device of claim 14, wherein the plurality support ribs are substantially symmetrical relative to the split.

* * * * *